United States Patent [19]

Piechota, Jr. et al.

[11] Patent Number: 4,590,065
[45] Date of Patent: May 20, 1986

[54] STABLE FLAVOR-CONTAINING DENTIFRICE

[75] Inventors: Stanley E. Piechota, Jr., Somerset; Dorinda A. Sparacio, Edison, both of N.J.

[73] Assignee: Colgate-Palmolive Company, New York, N.Y.

[21] Appl. No.: 724,377

[22] Filed: Apr. 18, 1985

[51] Int. Cl.[4] .................. A61K 7/16; A61K 7/18; A61K 31/79
[52] U.S. Cl. ........................ 424/49; 424/52; 424/58; 424/80; 514/963; 206/524.1; 206/524.4
[58] Field of Search .............. 424/49, 80; 426/651; 514/963; 206/524.1, 524.4

[56] References Cited

U.S. PATENT DOCUMENTS

| Re. 29,634 | 5/1978 | Roberts et al. | 424/57 |
|---|---|---|---|
| 2,783,182 | 2/1957 | Nelson | 424/80 |
| 3,169,905 | 2/1965 | Lambert | 424/80 |
| 3,216,579 | 11/1965 | Shelanski et al. | 424/80 |
| 3,257,276 | 6/1966 | Broh-Kahn | 424/80 |
| 3,431,208 | 3/1969 | Bailey | 252/106 |
| 3,725,541 | 4/1973 | Queuille et al. | 424/80 |
| 3,736,274 | 5/1973 | Schoenholz et al. | 424/80 |
| 3,935,306 | 1/1976 | Roberts | 424/49 |
| 3,957,964 | 5/1976 | Grimm | 424/10 |
| 3,998,974 | 12/1976 | Zaffaroni | 426/534 |
| 4,071,614 | 1/1978 | Grimm | 424/49 |
| 4,089,943 | 5/1978 | Roberts et al. | 424/49 |
| 4,307,076 | 12/1981 | Harvey et al. | 424/49 |
| 4,376,762 | 3/1983 | Hauschild et al. | 424/49 |
| 4,443,564 | 4/1984 | Hauschild et al. | 523/105 |

*Primary Examiner*—Shep K. Rose
*Attorney, Agent, or Firm*—Robert L. Stone; Murray M. Grill; Herbert S. Sylvester

[57] ABSTRACT

A dentifrice composition that reduces the migration/absorption of flavor into plastic packaging materials, containing a flavor oil in combination with about 5.0%–50.0% and preferably 12.0% by weight of the total flavor oils of polyvinyl pyrrolidone (PVP), dispersed in a dental vehicle. The dentifrice composition may be in the form of a paste, cream or gel. It is essential that the flavor oil and PVP be premixed prior to its addition to the dentifrice composition, preferably as a final step in its formulation.

16 Claims, No Drawings

STABLE FLAVOR-CONTAINING DENTIFRICE

BACKGROUND OF THE INVENTION

This invention relates to reduction of migration and absorption of flavor from a dentifrice into plastic packaging materials, by including in the dentifrice polyvinyl pyrrolidone additive in small amounts, by forming a combination of flavor oil and PVP prior to its addition to the dentifrice.

The use of polyvinyl pyrrolidone (PVP) in dentifrice compositions as a thickener and binder is well known in the prior art as disclosed in U.S. Pat. No. 4,307,076 in an amount of at least 3% by weight; in U.S. Pat. Nos. 3,429,963, 3,970,747, 3,120,469, and 4,223,003 as one of several gelling agents; and in U.S. Pat. No. 4,376,762 as the water soluble binder in combination with a water insoluble binder in providing visible speckles in dentifrices.

Polyvinylpyrrolidone has also been used as an antistaining agent in chlorophyll-containing dentifrice compositions as disclosed in U.S. Pat. No. 2,783,182, and British Pat. Nos. 739,936 and 741,315.

However, the use of PVP in amounts representing 5% to 50% by weight of the total flavor oils, in combination with flavor oils, in dentifrice compositions, to minimize flavor loss in plastic packages has not been disclosed in the prior art.

SUMMARY OF THE INVENTION

It has unexpectedly been found that dentifrice compositions comprising flavor oil in combination with PVP has the unique property of reducing flavor migration and absorption into plastic packaging materials.

Accordingly, a primary object of present invention is to provide a flavor-containing dentifrice composition that reduces the migration and absorption of flavor into plastic packing material.

Another object of present invention is to provide a flavor-stabilized dentifrice composition containing a flavor oil in combination with 5% to 50% PVP by weight of the total flavor oils.

Still another object of present invention is to provide a plastic-packaged flavor oil-containing dentifrice stabilized against flavor loss, containing about 12% PVP by weight of the total flavor oils, which minimizes contact and migration of the flavor onto the inner surfaces of the package.

Another object of present invention is to provide a dentifrice in paste, gel or cream form containing flavor oils in combination with 5% to 50% PVP by weight of the total flavor oils.

Additional objects, advantages and novel features of the invention will be set forth in part of the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects and in accordance with the present invention, as embodied and broadly described herein, the novel dentifrice of this invention, which has improved stability against flavor loss into plastic package components, comprises a flavor oil in combination with 5.0%–50% PVP by weight of the total flavor oils dispersed in a dental vehicle. The composition is in the form of a paste, gel, or cream dentifrice formulation.

More specifically, this invention relates to a plastic-packaged dentifrice composition stabilized against flavor loss comprising the combination of a flavor oil and about 12.0% PVP by weight of the total flavor oils in the form of a premix, dispersed in a dental vehicle. This premix is preferably added to the dentifrice formulation as a final step.

The use of plastic laminate tubes and plastic pump dispensers in toothpaste packaging has resulted in a problem not usually encountered with metal packages, the absorption of dentifrice flavor components into the plastic packaging material. Manufacturers of dentifrice packages have attempted to minimize flavor absorption by using less permeable plastic packaging compositions wherever possible, but design and engineering constraints prohibit the development of packages that are totally immune to flavor absorption. At least one toothpaste manufacturer has increased the level of flavor in their products, at extra cost, to make up for the flavor lost in the plastic package. An ideal remedy for flavor absorption into plastic would be to tie up the flavor oil chemically in the toothpaste formulation to minimize contact and migration of the flavor onto the inner surfaces of the package.

It has now been found that the flavor loss from a plastic-packaged dentifrice is reduced when polyvinyl pyrrolidone is combined with the dentifrice flavor oil and said combination is incorporated into the dentifrice composition, preferably as the final step in the formulation of the dentifrice.

An experiment was conducted to determine the effect on flavor emulsification in a conventional toothpaste formula when the flavor oil is first gelled with PVP. The formula aqueous phase consisting of water, glycerine, sodium MFP, tetra sodium pyrophosphate, sodium benzoate and sodium lauryl sulfate was prepared and divided into two equal parts. Flavor oil was added to one part (0.84% level on a finished formula basis) and the same flavor oil gelled with 0.1% PVP (representing 12.0% of the flavor oils) was added to the other part, both under moderate agitation. After standing for a few hours, the flavor oil gelled with 0.1% PVP, separated from the aqueous phase and formed a distinct top layer while the unmodified flavor oil remained well dispersed. PVP remains bound with the flavor oil, instead of becoming solubilized into the aqueous phase. It became apparent that flavor oil tied up with PVP may reduce flavor migration/sorption into plastic. Although the PVP/flavor oil gel separates in the aqueous phase, when the remaining formula components consisting of conventional gum binders and abrasives, are added to complete the dentifrice composition, the PVP/flavor oil gel remains evenly dispersed in the compositions.

The PVP used in present invention may be of any molecular weight grade or physical form. PVP is a water soluble polymerized N-vinyl-pyrrolidone to any desired molecular weight or degree of polymerization, having an average molecular weight from about 5,000 to approximately 1,000,000. It is conventionally in the form of a solid powder or flake, but can also be supplied in an aqueous solution. Although the PVP may be of any molecular weight, it is preferable to use high molecular weight PVP, above 50,000 and preferably within the range of about 60,000 to approximately 1,000,000. It is soluble in cold water and in a variety of organic alcohols, acids, ether-alcohols, ketone-alcohols, chlorinated hydrocarbons, esters and ketones; but is insoluble in hydrocarbons, flavor oils and some ethers, chlorinated hydrocarbons, ketones and esters. The amount of PVP utilized to tie up the flavor oil may be within the range of 5.0% to 50.0% by weight of the flavor oils and preferably about 12.0% by weight of the flavor oils. Although the exact nature of the mechanism by which the PVP ties up the flavor oil is not known, it is believed to form a coacervate with the flavor oil, i.e. an aggregate of colloidal droplets held together by electrostatic forces. This resembles a gel in appearance, but is not a true gel. However, the combination of flavor oil and PVP will be referred to as a gel. The formation of a coacervate of PVP and flavor oil is unexpected and unique. The preference of the PVP to combine with the flavor oil instead of dissolving in the aqueous medium is unexpected, because of the insolubility of the PVP in flavor oils, which presupposes no interaction therebetween.

Any suitable flavor oil or mixture thereof may be used in this invention. Examples of flavor oils include oils of spearmint, peppermint, wintergreen, sassafras, clove, sage, eucalyptus, marjoram, cinnamon, lemon and orange. The flavoring oils are water-insoluble and are emulsified into the dentifrice formulation under moderate agitation in amounts of 0.01 to 5% by weight and preferably about 0.5–3% by weight.

The dental base or vehicle utilized in present invention may be in the form of a paste or gel, comprising known ingredients conventionally used in the dentifrice art.

Paste or gel dentifrices may be based on aqueous or substantially non-aqueous systems. The former will usually include substantial proportions of finely divided, solid polishing agent, surface active agent, gelling agent and some nonaqueous vehicle, e.g., glycerol, sorbitol, and will be opaque, whereas the latter type will often be a clear gel, containing a minor proportion of a visually clear particulate solid polishing agent, a larger proportion of non-aqueous vehicle, surface active agent and gelling agent, with a minor proportion of water often being present.

The surface active agent, or detergent, present in the dentifrice may sometimes be cationic or amphoteric but will usually be anionic or nonionic. Of these compounds, the anionics are the most preferred. The anionic detergents or surface active agents also usually serve as foaming agents. Among the useful anionic detergents may be mentioned the higher fatty acid monoglyceride monosulfates, such as the sodium salts of the monosulfated monoglycerides of hydrogenated coconut oil fatty acid; higher alkyl sulfates, such as sodium lauryl sulfate; higher alkyl aryl sulfonates, such as sodium linear dodecyl benzene sulfonate; higher olefin sulfonates, such as sodium higher olefin sulfonate in which the olefin group is 12 to 21 carbon atoms; higher alkyl potassium sulfoacetates; higher fatty acid esters of 1,2-dihydroxypropane sulfonates, magnesium salt; the substantially saturated higher aliphatic acyl amides of lower aliphatic aminocarboxylic acid alkali metal salts, such as those having 12 to 16 carbon atoms in the fatty acyl radicals, higher alkyl poly-lower alkoxy (of 10 to 100 alkoxies) sodium sulfates; higher fatty acid sodium and potassium soaps of coconut oil and tallow, and the like. As is noted, most frequently the detergents are sulfated or sulfonated compounds. Examples of useful anionic amides which may be employed are N-lauroyl sarcosine and the sodium, potassium and ethanolamine salts of N-lauroyl-, N-myristoyl, and N-palmitoyl sarcosines. In the above descriptions, "higher" refers to chain lengths of 12 to 22 carbon atoms, preferably of 12 to 18 carbon atoms and most preferably of 12 to 16 carbon atoms. Lower means 2 to 4 carbon atoms, preferably 2 to 3 carbon atoms and most preferably, two carbon atoms.

The nonionic detergents include those containing chains of lower alkylene oxide, e.g., ethylene oxide, propylene oxide, in which there are present from 10 to 100 or more moles of lower alkylene oxide. Among such materials are the block co-polymers of ethylene oxide, propylene oxide and propylene glycol, sold as Pluronics; the alkyl phenyl polyethoxy ethanols, sold as Igepals; mixed co-polymers of ethylene oxide and propylene oxide, sold as Ucons; and various other well known nonionics derived from fatty alcohols or acids and polyethylene oxide. The amphoteric or ampholytic agents include long chain (alkyl) amido-alkylene-alkalated amine derivatives, such as "Miranols", e.g. Miranol $C_2M$; and cationic germicidal detergents, such as diisobutylphenoxyethoxyethyl dimethyl benzyl ammonium chloride, benzyl dimethyl stearyl ammonium chloride; and tertiary amines having a higher fatty alkyl group and two polyoxyethylene groups attached to the nitrogen thereof.

The detergents constitute about 0.5–5% and preferably up to 3% by weight of the dentifrice composition.

Toothpastes, and dental gels conventionally contain substantially water insoluble polishing agents or abrasives which are compatible with the formulation, in amounts from about 15–75% by weight of the total gel or paste formulation. Suitable polishing agents include anhydrous dicalcium phosphate, dicalcium phosphate dihydrate, tricalcium phosphate, insoluble sodium metaphosphate, crystalline silica, colloidal silica, complex aluminosilicates, aluminum hydroxide (including alumina trihydrate or hydrated alumina), magnesium phosphate, magnesium carbonate, calcium carbonate, calcium pyrophosphate, bentonite, talc, calcium silicate, calcium aluminate, aluminum oxide, aluminum silicate, and silica xerogels. Most of the polishing agents mentioned are most useful in the preparation of opaque dentifrices but some of them, such as colloidal silicas, especially the silica xerogels which include a low combined alumina content, and complex sodium aluminosilicates, may be utilized in the manufacture of clear gel dentifrices, because their indexes of refraction approximate those of the rest of the dentifrice constituents in an appropriate vehicle.

In dental gel or toothpaste dentifrice formulations, the liquids and solids should necessarily be proportioned to form a creamy mass of desired consistency, which for example is extrudable from a collapsible laminate tube or pump dispenser. In general, the liquids in the dental gel or toothpaste will comprise chiefly water, glycerine, sorbitol, polyethylene glycol, or propylene glycol 400, including suitable mixtures thereof. It is advantageous usually to use a mixture of both water, and a humectant such as glycerine, or sorbitol or mixtures thereof. The total liquid content will generally be about 20–75% by weight of the formulation. It is preferred to use also a gelling agent in dental creams such as the natural and synthetic gum-like materials, e.g. Irish Moss, gum tragacanth, sodium carboxymethylcellulose, polyvinylpyrrolidone, xanthan gum, or starch. Irish Moss and sodium carboxymethylcellulose, are compatible particularly and are preferred gelling agents. The gum content is usually in an amount up to about 10% and preferably about 0.3-5% by weight of the formulation. Fillers such as pyrogenic silica and silica aerogel may also be used, typically in amounts up to about 10% by weight to supplement the gelling agent. These colloidal silica aerogels which include Syloids 244 and 266 and Aerosil, and the pyrogenic silica sold as Cab-O-Sil may be used as gelling and thickening agents.

Various other materials may also be incorporated into the dental vehicle. Examples thereof are fluorine-containing compounds such as stannous fluoride, potassium stannous fluoride (SnF$_2$KP), sodium hexafluorostannate, stannous chlorofluoride, sodium fluorozirconate and sodium monofluorophosphate. These materials, which dissociate or release fluorine-containing ions in water, may be present in the dental vehicle in an effective, but nontoxic amount, usually within the range of about 0.1-5% by weight. Other additives include preservatives such as sodium benzoate, chlorophyll compounds, silicones, ammoniated materials such as urea and diammonium phosphate, antibacterial agents such as benzethonium chloride and other quaternary antibacterial compounds, sweeteners such as sodium saccharin, coloring. These additives may be used in amounts which do not adversely affect the properties and characteristics of the dentifrice in accordance with present invention. Each constituent may be present in minimal amounts of up to a maximum of 5% by weight and preferably up to 1% by weight of the formulation.

The dentifrice of this invention is prepared by conventional methods of making toothpaste, and dental creams. More specifically, a toothpaste may be prepared by forming a gel with carboxymethylcellulose and water, adding thereto with mixing the powdered materials and humectant, followed by the addition with mixing of polishing agent and then the surfactant, and then the flavor oil premixed with the PVP, and tubing the final mixture or packaging in plastic material.

In the practice of this invention to promote oral hygiene, the dentifrice according to this invention is applied regularly to dental enamel by brushing the teeth for 30-90 seconds at least once daily.

DETAILED DESCRIPTION OF THE INVENTION

The following examples are further illustrative of the nature of the present invention, but it is understood that the invention is not limited thereto. The compositions are prepared in the usual manner and all amounts and proportions referred to herein and in the appended claims are by weight unless otherwise specified. The flavor oil is admixed with the PVP prior to the addition of this gelled combination to the dentifrice formula.

EXAMPLES 1 and 2

TOOTHPASTE

| Ingredient | Ex. 1 % | Ex. 2 % |
|---|---|---|
| Deionized Water | 24.49 | 24.39 |
| Glycerine (99.5%) | 22.00 | 22.00 |
| Sodium Monofluorophosphate | 0.76 | 0.76 |
| Carboxymethylcellulose 7MF | 1.00 | 1.00 |
| Tetrasodium Pyrophosphate | 0.25 | 0.25 |
| Sodium Saccharin | 0.20 | 0.20 |
| Sodium Benzoate | 0.50 | 0.50 |
| Sodium Lauryl Sulfate | 1.20 | 1.20 |
| Dicalcium Phosphate Dihydrate | 48.76 | 48.76 |
| Flavor[1] | 0.84 | 0.84 |
| Polyvinylpyrrolidone[2] | — | 0.10 |

[1]Consisting predominately of oil of peppermint, oil of spearmint, menthol.
[2]Luviskol K-90, BASF, Inc., Average M.W. >1,000,000

The effect on flavor absorption into plastic between unmodified flavor oil and flavor oil gelled with 0.1% PVP in a toothpaste based on dicalcium phosphate dihydrate as abrasive/polishing component was measured instrumentally on a gas chromatograph. One method measures the quantity of flavor released into the headspace of a toothpaste package; and another method measures the quantity of flavor absorbed by a section of a laminate toothpaste tube.

The quantity of flavor released into the headspace of a toothpaste package measured 2.96±0.11 G.C. units of flavor for Example 1, and 2.74±0.08 G.C. units for Example 2 (0.% PVP). These results are statistically significantly different at the 99% confidence level.

Example 2 with 0.1% PVP inhibits the release of flavor from the dentifrice into a laminate tube by 16%, which is significant at the 95% confidence level, when compared to Example 1 without PVP.

EXAMPLES 3-6

| Ingredient | Dentifrice Gel | | | |
|---|---|---|---|---|
| | Ex. 3 | Ex. 4 | Ex. 5 | Ex. 6 |
| Sorbitol (70%) | 41.49 | 41.39 | 41.10 | 41.00 |
| Glycerine | 25.0 | 25.0 | 18.0 | 18.0 |
| Silica containing low combined alumina | 18.0 | 18.0 | 18.0 | 18.0 |
| Silica Thickener | 5.5 | 5.5 | 5.5 | 5.5 |
| Polyethylene Glycol 600 | 3.0 | 3.0 | 3.0 | 3.0 |
| Deionized Water | 3.0 | 3.0 | 3.0 | 3.0 |
| Sodium Lauryl Sulfate | 1.2 | 1.2 | 1.2 | 1.2 |
| Sodium Monofluorophosphate | 0.76 | 0.76 | 0.76 | 0.76 |
| Flavor[3] | 0.69 | 0.69 | — | — |
| Sodium Benzoate | 0.50 | 0.50 | 0.50 | 0.50 |
| Sodium Carboxymethyl Cellulose | 0.35 | 0.35 | 0.35 | 0.35 |
| Sodium Saccharin | 0.30 | 0.30 | 0.20 | 0.20 |
| FD % C Blue #1 (1% Aqueous) | 0.20 | 0.20 | — | — |
| Titanium Dioxide | 0.01 | 0.01 | 0.5 | 0.5 |
| Polyvinylpyrrolidone | — | 0.10 | — | 0.10 |
| Flavor[1] | — | — | 0.89 | 0.89 |

[3]Consisting predominately of oil of spearmint, oil of peppermint, anethole.

Each of the silica abrasive gel formulae was evaluated in aluminum tubes, laminate tubes and pump dispensers under accelerated conditions. After nine weeks of aging no form of separation/leakage was seen in the PVP formulae while the formulae without PVP exhibited clip and cap wet in the tubes and piston wetness or button wetness in the dispenser. It appears that by tying up the flavor oil, the reaction that causes separation/leakage of silica formulae, as well as a reduced flavor loss in the laminate tubes and pump dispensers is significantly decreased.

This unique combination of flavor oil and PVP has the unexpected ability of reducing flavor loss into plastic package components, as well as reducing separation/leakage of silica formulae in tubes and dispensers.

It is understood that the foregoing detailed description is given merely by way of illustration and that variations may be made therein without departing from the spirit of the invention. The "Abstract" given above is merely for the convenience of technical searchers and is not to be given any weight with respect to the scope of the invention.

We claim:

1. A plastic packaged toothpaste or gel dentifrice composition free of free flavor oil tending to migrate to, and be absorbed by plastic packaging and thereby having improved stability against flavor loss by migration and abosrption of free flavor oil into plastic package components comprising 0.01–5% by weight of a flavor oil colloidally bound with about 5.0% to 50.0% by weight of the total flavor oils of polyvinylpyrrolidone, dispersed in a flavor-free dental vehicle.

2. The dentifrice according to claim 1, wherein the flavor oil constitutes about 0.5–3.0% by weight of the composition.

3. The dentifrice according to claim 1, wherein the polyvinylpyrrolidone has an average molecular weight of 5,000 to approximately 1,000,000.

4. The dentifrice according to claim 1, wherein the polyvinylpyrrolidone has an average molecular weight of about 60,000 to approximately 1,000,000.

5. The dentifrice according to claim 4, wherein the polyvinylpyrrolidone constitutes about 12.0% by weight of the flavor oils.

6. The dentifrice according to claim 5, which is in the form of a toothpaste containing about 15–75% by weight of a water insoluble polishing agent.

7. The dentifrice according to claim 5, which is in the form of a dental gel containing about 15–75% by weight of water insoluble silica polishing agent.

8. The dentifrice according to claim 1, containing about 0.5–5% surfactant.

9. The dentifrice according to claim 8, containing a liquid content of about 20–75% by weight of the composition.

10. The toothpaste according to claim 6, wherein the polishing agent is dicalcium phosphate dihydrate.

11. The dentifrice according to claim 7 wherein the polishing agent is silica containing combined alumina.

12. The dentifrice according to claim 9, containing about 0.1–5% by weight of a fluorine-containing compound capable of releasing fluorine ions in water.

13. The toothpaste according to claim 10, wherein the flavor oil comprises a mixture of oil of peppermint and oil of spearmint.

14. The dental gel according to claim 11, wherein the flavor oil is a mixture of oil of peppermint and oil of spearmint.

15. A method of preparing the dentifrice of claim 1, which comprises admixing the flavor oil and the polyvinylpyrrolidone to form a colloidal premix, followed by admixing said premix with the other formula components, and tubing or packaging the final mixture in plastic material.

16. A plastic packaged dentifrice composition having improved stability against flavor loss into plastic package components comprising a premix of flavor oil colloidally bound with about 5–50% by weight of the total flavor oils of polyvinylpyrrolidone, dispersed in a dental vehicle containing a water insoluble dental polishing agent.

* * * * *